United States Patent [19]

Wuendisch

[11] Patent Number: 5,000,950
[45] Date of Patent: Mar. 19, 1991

[54] AGENT FOR THE TREATMENT OF WOUNDS

[75] Inventor: Karl Wuendisch, Berlin, Fed. Rep. of Germany

[73] Assignee: Smith & Nephew Medical Ltd., England

[21] Appl. No.: 867,653

[22] Filed: May 28, 1986

Related U.S. Application Data

[63] Continuation of Ser. No. 640,476, Aug. 13, 1984, abandoned, which is a continuation of Ser. No. 513,562, Jul. 14, 1983, abandoned.

[30] Foreign Application Priority Data

Jul. 14, 1982 [DE] Fed. Rep. of Germany ....... 3226753

[51] Int. Cl.$^5$ ............................................. A61K 31/74
[52] U.S. Cl. .............................. 424/78; 424/DIG. 13
[58] Field of Search ........................................... 424/78

[56] References Cited

U.S. PATENT DOCUMENTS

| | | |
|---|---|---|
| 2,602,042 | 7/1952 | Abbott . |
| 3,935,099 | 1/1976 | Weaver et al. . |
| 3,981,100 | 9/1976 | Weaver et al. . |
| 3,985,616 | 10/1976 | Weaver et al. . |
| 3,997,484 | 12/1976 | Weaver et al. . |
| 4,043,952 | 8/1977 | Ganslaw et al. . |
| 4,090,013 | 5/1978 | Ganslaw et al. . |
| 4,094,832 | 6/1978 | Soederberg . |
| 4,094,833 | 6/1978 | Johansson et al. . |
| 4,225,580 | 9/1980 | Rothman et al. . |
| 4,226,232 | 10/1980 | Spence . |
| 4,287,177 | 9/1981 | Nakashima et al. . |
| 4,302,369 | 11/1981 | Elmquist . |
| 4,414,202 | 11/1983 | Silvetti . |
| 4,457,944 | 7/1984 | Conrad et al. ................ 424/358 |

OTHER PUBLICATIONS

Roempps Chemie-Lexikon, 7th Ed., Eng. translations of pp. 698, 1056, 1931, 1932, 2504, 2735, 2748, 3780 (1972).

*Primary Examiner*—Frederick E. Waddell
*Attorney, Agent, or Firm*—Jacobs & Jacobs

[57] ABSTRACT

A wound-treating composition comprising a graft copolymer is disclosed along with a method of using the same.

20 Claims, No Drawings

AGENT FOR THE TREATMENT OF WOUNDS

CROSS REFERENCE TO RELATED APPLICATIONS

This application is related to U.S. Ser. No. 714,222, filed March 27, 1985, and whose disclosure is incorporated by reference and a continuation of U.S. Ser. No. 640,476, filed Aug. 13, 1984, now abandoned, as a continuation of Ser. No. 513,562, filed July 14, 1983, now abandoned.

BACKGROUND OF THE INVENTION

Agents for the treatment of inflamed wounds are known. For example, in addition to conventional textile bandages, a product based on dextran has been utilized in wound treatment (U.S. Pat. No. 4,225,580). However, this material has the disadvantage that it is relatively difficult to apply and, in particular, that its removal from the wound causes relatively great difficulties since the small dextran grains readily stick to the edges of the wound.

In addition, U.S. Pat. No. 4,302,369 discloses a wound treatment based on a graft copolymer of starch and hydrolyzed polyacrylonitrile wherein the carboxy group H-atoms are substituted by aluminum cations. However, these also are disadvantageous.

SUMMARY OF THE INVENTION

It is an object of this invention to provide improved wound treatment agents and methods for their use.

Upon further study of the specification and appended claims, further objects and advantages of this invention will become apparent to those skilled in the art.

These objects have been attained based on the discovery that substantially more favorable properties as compared with the prior art agents for the same use, are displayed by agents for wound treatment containing 1–4% by weight (based on the agent's total weight) of a graft copolymer of starch and hydrolyzed polyacrylonitrile wherein the carboxy group hydrogen atoms are substituted by aluminum to an extent of 5–90%, in a 2–50% by weight aqueous, physiologically acceptable di- or polyhydroxyalkane solution.

DETAILED DISCUSSION

The graft copolymer of starch and hydrolyzed polyacrylonitrile whose carboxy group hydrogen atoms are substituted by aluminum to an extent of 5–90%, and which is utilized in the agent of this invention, can be prepared, for example, according to the disclosure of U.S. Pat. No. 4,302,369, by reacting, under the conditions set forth therein, a starch suspension with acetonitrile in the presence of a chemical initiator, such as cerium-ammonium nitrate, hydrolyzing the resultant graft copolymer with strong bases, and then reacting the same with aluminum salts. The thus-obtained product can then be dried, washed with alcoholic ammonia solution, and adjusted with hydrochloric acid to the desired pH of 6.0–7.5. However, on the other hand, it is also possible to purchase this product, for example, from the patentee, Henkel Corporation, Minneapolis, for example under the name SGP 157 M. In general, unless indicated otherwise herein, all details of the graft copolymer itself and its preparation are fully conventional as disclosed in U.S. Pat. No. 4,302,369 and 3,935,099, whose disclosures are incorporated by reference herein.

Graft copolymers exhibiting the following features are especially suitable for preparation of the agent of this invention: The weight ratio of starch component to the sum of acrylate and acylamido components is preferably 1:3 to 1:0.9; the molar ratio of carboxy groups to amido groups is preferably 2:1 to 9:1; preferably, 25 to 75 percent of the carboxyl groups are substituted by aluminum; and the particle size of the copolymer is preferably 0.01 to 0.5 mm.

Suitable dihydroxyalkanes include those of 2–6 carbon atoms, for example, 1,2-dihydroxyethane, 1,2-dihydroxypropane, 2,3-dihydroxybutane, or 3,4-dihydroxyhexane, etc.

Suitable polyhydroxyalkanes include those of the formula:

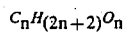

$$C_nH_{(2n+2)}O_n$$

wherein n includes the numbers 3–6, for example, glycerol, sorbitol, mannitol, adonitol, ribitol, dulcitol, erythritol, or xylitol, etc.

Suitable hydroxy-containing polyalkanes for preparing the agent of this invention include polyethylene glycols with a molecular weight of 200–600 (number average); and polypropylene glycol preferably of a number average molecular weight of 200–450.

The di- or polyhydroxyalkane is employed in the agent of this invention to an extent of up to 50% by weight (based on the total weight of the final agent of this invention), and preferably in a concentration of 10–30% by weight. The diols or polyols are preferably formulated with demineralized water for use in this invention.

The agents of this invention can be prepared in fully conventional fashion, e.g., the components can be uniformly blended, for example by means of an agitator, and sterilized by heating. Preferably, the agents of this invention are formulated to have the consistency of a paste.

Of course, all ingredients used in the agents of this invention must be pharmacologically acceptable, e.g., as listed in the U.S. Pharmacopia whose disclosure is incorporated by reference herein. All ingredients are per se conventional, e.g., as disclosed in Roempp's ChemieLexikon, 7th ed, Neumueller Ed, 1972, whose disclosure is incorporated by reference herein.

The agent for wound treatment of this invention is suitable, not only for the treatment of wounds in a narrow sense, but also in the broadest sense of this term, e.g., for the treatment of numerous secretionary inflammations or injuries of the skin or mucosa, e.g., as described for the wound treatment agents listed in the "Rote Liste—1980" [Red List—1980] issued by the Federal Association of the Pharmaceutical Industry [registered society], D-6000 Frankfurt/Main. Such diseases or injuries include, for example, cuts, stab wounds, lacerations, contusions, burns, frostbite, abrasions, sunburn, eczemas, hemorrhoids, etc.

The agent for wound treatment of this invention can additionally contain additives and auxiliary materials (e.g., fragrances) customary in such topical agents, and, moreover, active agents usually employed in these topical preparations. Typically, each of these is contained in amounts of 0.005–2 wt % based on the total weight of the agent. Such active agents include, for example, bacteriostats, e.g., sulfonamides (e.g., sulfadiacin, sulfatolamide, etc.); antibiotics (e.g., penicillin, neomycin, chloramphenical): etc.; antimycotic agents, e.g., salicylic acid and its derivatives (e.g., salicylichydroxamic acid or salicylicamide, etc.), micronacol, isoconacol, etc.; local anesthetics, e.g., esters of p-aminobenzoic acid (e.g., the methyl or ethyl ester), lidocain, etc.

The application of the agent of this invention is fully conventional for wound treatment agents, e.g., the agent can be applied to the location of the body to be treated, and optionally covered with gauze. It is conventionally periodically replaced when soiled or fully secretion loaded.

The agent of this invention is distinguished by an extraordinary suction pressure and consequently promotes rapid healing of the wound due to dehydration. Other soluble compatible agents can also be utilized in the agent of this invention. See, e.g., Roempps, supra.

Rapid healing is not impaired by the di- or polyhydroxyalkanes contained in the agent of this invention. These polyhydric alcohols effect a reduction in vapor pressure so that the agents of this invention do not dry out. This avoids the sticking together of wounds or wound edges so that the agent can be removed without complications or discomfort. Moreover, these polyhydric alcohols have the effect of rendering the gel preparation pastier and thus more easily applicable. The gel (graft copolymer) in the formulations of this invention can be sterilized in the usual way; its pH value is adjusted so that it is within the therapeutically especially desirable range of between 6.0 and 7.5.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2.000 g of graft copolymer SGP 157 M by Henkel Corporation, Minneapolis, is washed with methanolic ammonia solution and adjusted to pH 6.8 with dilute hydrochloric acid. The polymer is then blended under agitation with 68.00 g of demineralized water and 30.00 g of glycerol (DAB 8) until a pasty composition is obtained. The latter is sterilized in a pressurized autoclave at 125° C.

EXAMPLE 2

2.000 g of graft copolymer SGP 157 M by Henkel Corporation, Minneapolis, is washed with methanolic ammonia solution and adjusted to pH 6.8 with dilute hydrochloric acid. The polymer is then blended under agitation with 68.00 g of demineralized water and 30.00 g of polyethylene glycol, molecular weight 600, until a pasty composition is obtained. The latter is sterilized in a pressurized autoclave at 125° C.

EXAMPLE 3

2.000 g of graft copolymer SGP 157 M by Henkel Corporation, Minneapolis, is washed with methanolic ammonia solution and adjusted to pH 6.8 with dilute hydrochloric acid. The polymer is then blended under agitation with 78.00 g of demineralized water and 20.00 g of 1,2-dihydroxypropane until a pasty composition is produced. The latter is sterilized in a pressurized autoclave at 125° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aqueous agent for the treatment of a wound by application directly thereto, thereby facilitating healing by dehydration of the wound, and which can be removed without discomfort, comprising 1-4% by weight of a graft copolymer of starch and hydrolyzed polyacrylonitrile, 5-90 molar % of whose carboxy group hydrogen atoms have been substituted by aluminum cations; 2-50% by weight of a (poly)dihydroxyalkane or a polyhydroxyalkane; and water.

2. A wound treatment agent of claim 1 wherein the water is demineralized water.

3. A wound treatment agent of claim 1 comprising 10-30% by weight of the di- or polyhydroxyalkane.

4. A wound treatment agent of claim 1 comprising a dihydroxyalkane which is a glycol of 2-6 carbon atoms.

5. A wound treatment agent of claim 1 comprising a polyhydroxyalkane which is a polyol of the formula

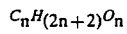

$$C_nH_{(2n+2)}O_n$$

wherein n is 3 to 6.

6. A wound treatment agent of claim 1 comprising a poly(hydroxyalkane) which is a water-soluble polyethylene glycol or polypropylene glycol.

7. A wound treatment agent of claim 6 comprising a polyethylene glycol of a molecular weight of 200-600 or a polypropylene glycol of a molecular weight of 200-450.

8. A wound treatment agent of claim 4 comprising 1,2-dihydroxyethane, 1,2-dihydroxypropane, 2,3-dihydroxybutane, or 3,4-dihydroxyhexane.

9. A wound treatment agent of claim 5 comprising glycerol, sorbitol, mannitol, adonitol, ribitol, dulcitol, erythritol, or xylitol.

10. A wound treatment agent of claim 1 comprising an effective amount of a topically active pharmacological agent.

11. A wound treatment agent of claim 10 wherein the active ingredient is a bacteriostat.

12. A wound treatment agent of claim 10 wherein the active ingredient is an antimycotic agent.

13. A wound treatment agent of claim 10 wherein the active ingredient is a local anesthetic.

14. A wound treatment agent of claim 1 which is a paste.

15. A method of treating a wound in a patient comprising treating the wound with an effective amount of the agent of claim 1.

16. A wound treating agent of claim 1 in the form of a sterile paste having a pH of between 6.0 and 7.5, wherein the water is demineralized water and wherein the (poly)dihydroxyalkane or polyhydroxyalkane is glycerol, a polyethylene glycol of a molecular weight of 200-600, or 1,2-dihydroxypropane.

17. A wound treating agent of claim 1, wherein the (poly)dihydroxyalkane or polyhydroxyalkane is glycerol.

18. A wound treating agent of claim 1, wherein the (poly)dihydroxyalkane or polyhydroxyalkane is 1,2-dihydroxypropane.

19. A wound treating agent of claim 1, wherein the (poly)dihydroxyalkane or polyhydroxyalkane is polyethylene glycol of a molecular weight of 200-600.

20. A method according to claim 15, wherein the wound treating agent is in the form of a sterile paste having a pH of between 6.0 and 7.5, wherein the water is demineralized water and wherein the (poly)dihydroxyalkane or polyhydroxyalkane is glycerol, a polyethylene glycol of a molecular weight of 200-600, or 1,2-dihydroxypropane.

* * * * *